United States Patent [19]

Trebing et al.

[11] Patent Number: 5,601,553
[45] Date of Patent: Feb. 11, 1997

[54] LOCKING PLATE AND BONE SCREW

[75] Inventors: Linda Trebing, Devon, Pa.; John Thalgott, Las Vegas, Nev.

[73] Assignee: Synthes (U.S.A.), Paoli, Pa.

[21] Appl. No.: 317,246

[22] Filed: Oct. 3, 1994

[51] Int. Cl.⁶ .......................... A61B 17/70; A61B 17/80; A61B 17/84
[52] U.S. Cl. ................ 606/61; 606/69; 606/73; 411/413; 411/399
[58] Field of Search ................... 606/60, 61, 69, 606/70, 71, 72, 73; 411/412, 413, 414, 386, 399

[56] References Cited

U.S. PATENT DOCUMENTS

| | | | |
|---|---|---|---|
| Re. 31,628 | 7/1984 | Allgower et al. | 606/69 |
| 2,380,724 | 7/1945 | Croks | 411/414 |
| 3,593,709 | 7/1971 | Halloran | 606/69 |
| 3,942,405 | 3/1976 | Wagner | 411/386 |
| 4,978,350 | 12/1990 | Wagenknecht | 606/72 |
| 5,085,660 | 2/1992 | Lin | 606/73 |
| 5,147,361 | 9/1992 | Ojima et al. | 606/69 |
| 5,364,399 | 11/1994 | Lowery et al. | 606/69 |

*Primary Examiner*—Michael Powell Buiz
*Assistant Examiner*—Scott B. Markow
*Attorney, Agent, or Firm*—Fish & Richardson P.C.

[57] ABSTRACT

A bone plate for stabilizing the anterior column of the spine has a lower curved surface and an upper surface having two intersecting planes in each of which is a screw hole, the axes of the holes being skewed relative to one another. A bone screw used to secure the plate, has a single start buttress thread near the tip and a two start machine thread near the head, the threads being continuous and of constant pitch.

16 Claims, 3 Drawing Sheets

LOCKING PLATE AND BONE SCREW

FIELD OF THE INVENTION

The present invention relates to a bone plate for the treatment of the spine, to a bone screw having particular applicability with said plate and to an orthopaedic system including the plate and screw.

BACKGROUND OF THE INVENTION

In the treatment of various spinal conditions, including the treatment of fractures, tumors and degenerative conditions, it is necessary to secure and stabilize the anterior column of the spine following removal of a vertebral body or part.

Following such removal made using a thoracotomy, thoracoabdominal or retroperitoneal approach, the normal anatomy is reconstructed using tricortical iliac crest or fibular strut grafts. It is then necessary to secure and stabilize the graft, desirably in such a manner as to permit rapid mobilization of the patient. Such objectives can be accomplished by a bone plate. However, to accomplish this service in the optimum manner, it is necessary that the plate be reasonably congruent with the bone to which it is applied, that it have as low a profile as possible, that it be firmly secured to the spinal column so that it is not torn out when the patient places weight and stress upon it and that it be capable of placement and fixation in a manner that is convenient for the surgeon.

In this context it is necessary to secure the plate to the spinal body and also, in some cases, to the graft. Conventionally, such attachment would be by the use of screws driven through screw holes in the plate into the bone. However, it is desirable in this instance not only to anchor the screw firmly in the spinal column in both the cortical and cancellous parts, but to have the screw firmly attached to the plate to prevent loosening of the screw/plate connection with changes in the bone.

SUMMARY OF THE INVENTION

The invention provides a bone plate, particularly useful as an anterior thoracolumbar locking plate comprising a body made of physiologically acceptable material such as stainless steel, titanium or a titanium alloy and having an upper surface and a lower surface, the lower surface being curved to conform to a cylindrical bone and the upper surface having two intersecting planes.

The bone plate is preferably curved in its longitudinal dimension. It has an anterior edge with a notch to make it easily grasped and manipulated with a forceps or similar tool and a posterior edge which is generally convex, there being threaded screw holes at the ends of the anterior and posterior edges. Preferably additional screw holes are provided which are not tapped but may have camming surfaces to permit fracture reduction. Such untapped holes may be used for temporary screws to retain the plate in place while permanent screw holes in the bone are precisely located and drilled. Preferably the axes of the screw holes at the ends of the screw holes at the ends of the plate edges are inclined to one another.

The invention further includes a bone screw, particularly adapted for use with the plate described, comprising a threaded shaft having a head and a tip, the threading comprising a single start buttress section at the tip end of the shaft and a two start machine screw thread at the head end of the shaft. The thread is of constant pitch, i.e. the linear or axial advance of the thread, per revolution, is constant over the length of the thread. The extreme tip of the shaft is pointed, unthreaded and provided with self-tapping end flutes.

The invention further includes a bone fixation system including a plate and a screw as described. Preferably the major diameter of the cancellous bone thread, i.e. the buttress thread is greater than the minimum diameter of the female thread in the threaded plate holes so that the starting point of the machine thread on the screws is aligned with the internal thread of the plate hole.

In yet another aspect the invention includes a method for applying a bone plate having a threaded screw hole and an unthreaded screw hole to a bone which comprises positioning the plate adjacent the bone surface temporarily fixing the plate to the bone surface by means of a bone screw through the unthreaded hole and then securing the plate to the bone by inserting a screw through the threaded screw hole in engagement with the threads in said hole.

The invention will be further described with reference to the drawings in which.

DETAILED DESCRIPTION OF THE INVENTION

Figure 1:
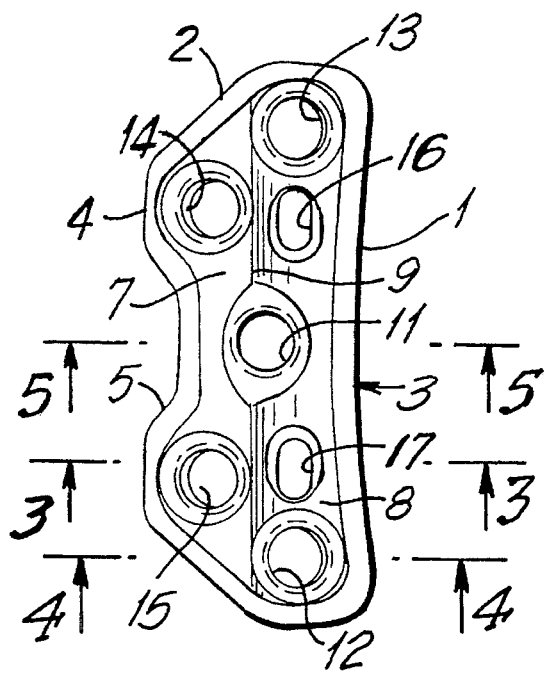
FIG. 1 is a top plan view of a plate according to the invention.
Figure 2:
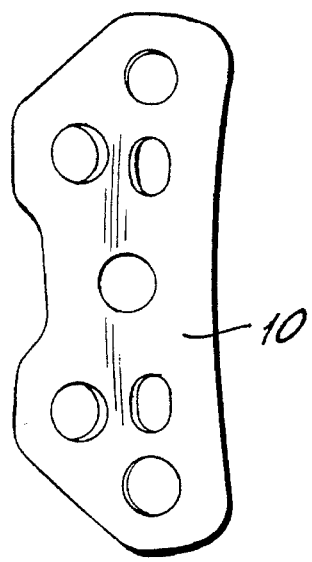
FIG. 2 is a bottom plan view of a plate according to the invention.
Figure 3:
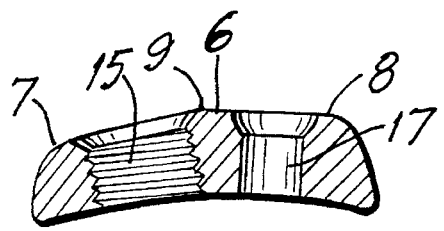
FIG. 3 is vertical section along the line 3—3 of FIG. 1.

Referring to FIGS. 1–3, a plate according to the invention comprises a body 1 normally of a biocompatible metal, such as stainless steel, titanium or a titanium alloy, and has a bevelled, rounded periphery 2. The posterior edge 3 of the plate is slightly curved to follow the shape of the spinal column. The anterior edge 4 is tapered inwardly and has a notch 5 to facilitate handling the plate with a tool such as a forceps. As shown in FIG. 3, both edges are smoothly rounded.

Figure 4:
FIG. 4 is a vertical section along the line 4—4 of FIG. 1.
Figure 5:
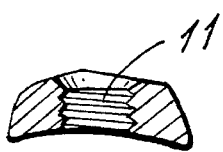
FIG. 5 is a vertical section along the line 5—5 of FIG. 1.

As shown in FIGS. 3–5, the plate transverse cross-section is curved to follow the bone surface. The upper plate surface 6 is bi-faceted or biplanar, with an anterior plane 7 and a posterior plane 8 meeting to form a central ridge 9, which, as shown in FIG. 1, extends down the long dimension of the plate. The bottom surface 10 of the plate, that intended for application to the bone, is, as indicated in FIGS. 2–5, a smooth, curved surface, preferably cylindrical.

The plate is provided with a plurality of threaded screw holes 11–15, five in the example shown in FIGS. 1 and 2, for locking screws. All are chamfered at the upper surface of the plate. Screw hole 11 is centrally located. Screw holes 12 and 13 are located at the extreme ends of the plate on the posterior side and screw holes 14 and 15 are positioned at the ends of notch 5, on the anterior side.

The axes of screw holes 14 and 15 are normal to the anterior plane 7 of the plate and the axes of holes 12 and 13 are normal to the posterior plane 8. Thus, the axes of adjacent holes 12 and 15, and 13 and 14, are inclined to one another or skewed. This creates a conical bone plug, rendering the plate more difficult to dislodge under load.

Central hole 11 is drilled straight through the plate, i.e. its axis is normal to a plane A—A (FIG. 3) tangent to the cylindrical bottom surface of the plate at the mid-point of the plate.

Figure 10:
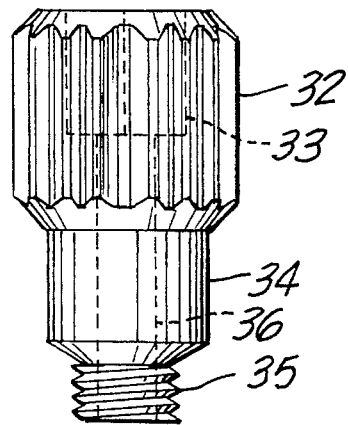
FIG. 10 is a view in side elevation of a drill guide for use with plates according to the invention.

It will be understood that the number of plate holes for locking screws may vary. In particular there may be several holes, for example, three, like hole 11, down the middle of the plate. Such a plate is shown in FIG. 10.

Figure 6:
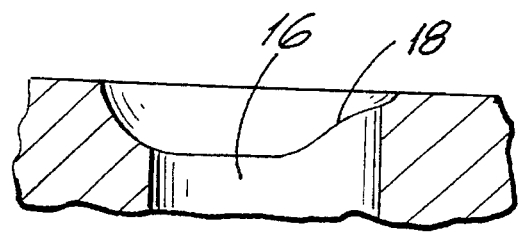
FIG. 6 is a fragmentary view in vertical section showing the profile of the hole 17 of FIG. 1.

In addition to the holes for locking screws, the plate is provided with two holes 16, 17 for temporary screws. As shown in FIG. 6, these holes 16 and 17 may be elongated with a camming surface 18 to enable the hole to be used to aid in compressing graft material. See Algower et al. U.S. Pat. No. Re. No. 31,628.

Figure 7:
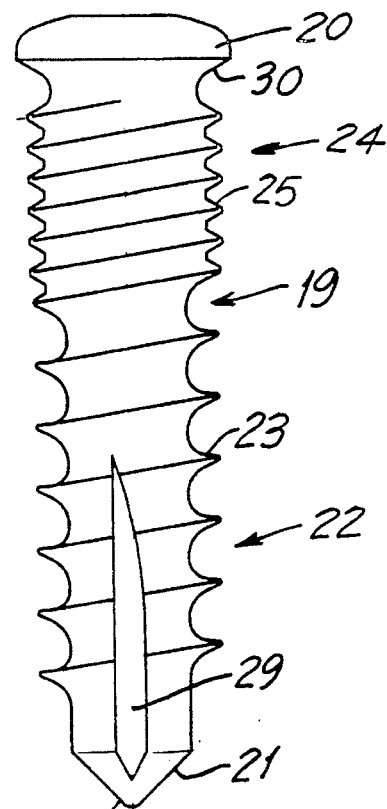
FIG. 7 is a view in elevation of a bone screw according to the invention.
Figure 8:
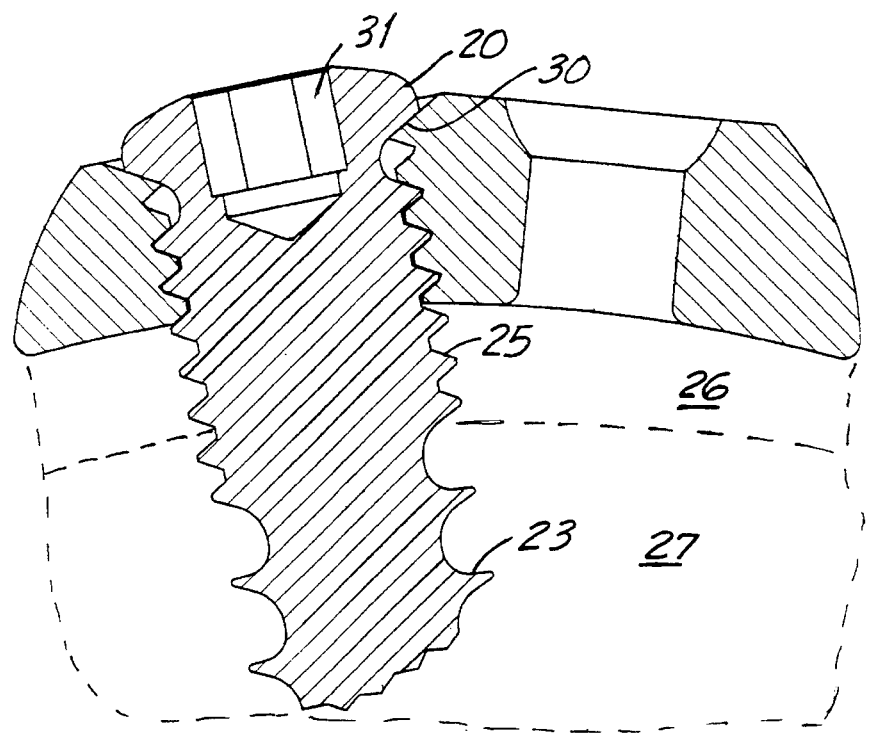
FIG. 8 is a fragmentary view in vertical section of a plate according to the invention secured in a bone by a bone screw according to the invention.

Plates according to the invention are preferably used with locking screws of the type illustrated in FIGS. 7 and 8. Referring to those figures, in this aspect the invention comprises a screw with shaft 19 having a head 20 and a tip 21. The shaft 19 is threaded, the lower part 22 (i.e., the part nearest the tip) being provided with a one-start buttress thread 23 and the upper part 24 (the part nearest the head) being provided with a two-start machine screw thread 25. The threads are synchronized to produce a constant and continuous lead over the entire length of the screw. The pitch is constant over both threads in the sense that the axial movement for one rotation of the screw is the same for both threads. When used with the plate according to the invention, the internal thread of the plate holes 11–15 is a two-start thread selected to mate with the thread of the screw. Because the pitch is constant, the plate will remain in its original position on the bone and there is no tendency to strip the thread out of the bone as the screw is advanced through the plate holes.

As shown in FIG. 8, the length of the machine thread is sufficient to engage the cortex 26 of the bone, while the buttress thread engages cancellous bone 27.

Preferably the major diameter of the cancellous bone thread, i.e. the buttress thread, is greater than the minimum diameter of the female thread in the plate so that the starting point of the machine thread of the screw is readily aligned with the thread of the plate.

The tip of the screw is conically pointed as at 28 and is provided with self-tapping flutes 29 (normally three in number).

The bottom surface 30 of the screw head is preferably conical. The upper surface is preferably spherical and is provided with means such as hexagonal socket 31 for receiving a wrench or other tool.

Figure 9:
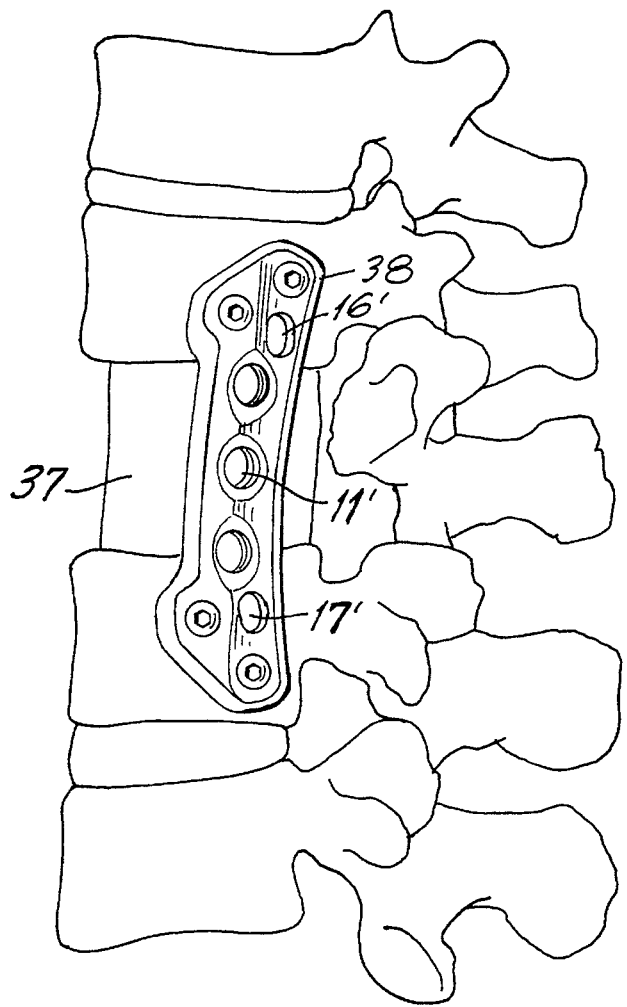
FIG. 9 is a schematic view showing the plate according to the invention secured to a spinal column with screws according to the invention.

A typical use of the plate and screw according to the invention is illustrated in FIG. 9. As shown there a portion of the spinal column has been removed, a graft 37 inserted and a plate 38 according to the invention applied across the graft site to provide rigid fixation of the anterior spinal column.

Assuming the surgeon has chosen his approach, exposed the spinal column, decompressed the spinal end, and applied the graft material, a threaded drill guide is inserted into the threaded center hole 11' of the plate. The drill guide may be of any conventional design. A suitable form is shown in FIG. 10. It has an upper section 32 knurled to facilitate manipulation and having an inner socket 33 to receive a wrench or like tool. The lower section 34 has a tip 35 of reduced diameter. The tip is threaded to engage with the internal threads of plate holes 11–15. A bore hole 36 runs through the guide for receiving a suitable drill (not shown).

With the drill guide inserted, the plate is positioned on the posterior quarter of the vertebral body using the drill guide as a handle and a forceps or plate holder. Care must be taken that all screws will be placed in the vertebral body. A lateral x-ray should be obtained to see that no screws violate the spinal canal.

Using a drill guide, for example, a guide of the design shown in Klaue U.S. Pat. No. 4,493,317, holes are drilled through the temporary screw holes 16' and 17'. Temporary screws are then inserted and tightened. The temporary screws compress the graft site and anchor the plate firmly to the bone. The drill guide is then removed from the center hole 11' and drill guides are inserted in the posterior holes of the plate. Holes are then drilled through the posterior holes. Locking screws according to the invention are then inserted in the posterior holes.

The temporary screws are then removed from holes 16' and 17'. Threaded drill guides are then inserted into the anterior holes, holes are drilled, the guides removed and screws according to the invention inserted.

If desired, additional locking screws may be inserted through the center plate hole or holes to secure the graft, using the procedure described above.

Although the use of the screw according to the invention has been described in connection with the specific plate of the invention, it will be apparent to those skilled in the art that it may be used advantageously with various other implants having suitably threaded screw holes including, for example, anterior and posterior spinal plates and spinal rod connectors.

What is claimed is:

1. A bone plate comprising an upper surface and a lower surface for application to a bone, the lower surface being curved to conform to a cylindrical bone and the upper surface having two flat intersecting planes, a first screw hole having an axis normal to one of said intersecting planes and a second screw hole having an axis normal to the other intersecting plane, said planes providing directional guides for insertion of screws in said holes.

2. The bone plate claimed in claim 1 and having a third screw hole which is unthreaded and furnished with a camming surface.

3. A bone plate for stabilizing the anterior column of the spine comprising an elongated body of physiologically acceptable metals having a longitudinal axis having a bottom surface curved about its longitudinal axis and having an anterior edge and a posterior edge extending generally parallel to the longitudinal axis, said anterior edge having a notch and screw holes at the ends of said notch, the posterior edge being concave and extending in a continuous uninterrupted curve in a plane containing the longitudinal axis, there being screw holes at the ends of said posterior edge.

4. The bone plate claimed in claim 3, said screw holes being threaded.

5. The bone plate claimed in claim 4 and comprising a plurality of unthreaded screw holes.

6. The bone plate claimed in claim 1 wherein said screw holes are threaded to receive locking screws, said plate comprising at least one additional hole, unthreaded, to receive a temporary anchoring screw.

7. The bone plate claimed in claim 6, said plate having an anterior edge and a posterior edge, said anterior edge having a notch for receiving a manipulation instrument.

8. The bone plate claimed in claim 7 wherein said posterior edge is concave and extends in a continuous uninterrupted curve.

9. A bone plate comprising an upper surface and a lower surface, the lower surface being curved for application to a bone and the upper surface having two flat intersecting planes, in combination with at least one screw hole in each of the planes of said upper surface, said screw holes having axes which are skewed with respect to one another and in separate planes, each axis being normal to the plane of the surface on which it is situated, the planes providing a directional guide for insertion of screws into said screw holes.

10. The bone plate claimed in claim 9 and also including a plurality of elongated screw holes having camming surfaces.

11. A bone screw comprising a shaft, a head and an unthreaded pointed tip, said shaft having an upper section adjacent the head and a lower cylindrical section adjacent the tip, the lower section having a first unthreaded part next to the tip and a second part having a single start buttress thread, and the upper section having a two-start machine screw thread, the threads taken as a whole being of constant pitch and the lead being continuous over both threads, the minor diameter of said machine screw thread being greater than the minor diameter of said buttress thread.

12. The screw claimed in claim 8 and having cutting plates adjacent said tip.

13. An orthopaedic fixation system for use in spinal surgery comprising a bone plate having a plurality of threaded screw holes for receiving locking screws and a plurality of locking screws, each of said screws having a section of single start buttress threads and a section of two-start machine threads the lead being continuous over said two sections.

14. The orthopaedic fixation system claimed in claim 13 wherein the major diameter of the buttress thread is greater than the minor diameter of the thread in the threaded screw holes.

15. An orthopedic fixation system for use in spinal surgery comprising a bone plate having a lower surface for application to the spinal column, an upper surface having two flat intersecting planes and a threaded screw hole in each of said planes, each of said screw holes having an axis normal to the plane on which it is situated, in combination with a screw for each of said screw holes, each of said screws having a buttress thread for engagement with cancellous bone and a machine screw thread for engagement with said screw holes and cortical bone, the planes providing a directional guide for insertion of screws into said screw holes.

16. A method for applying a bone plate having a threaded screw hole and an unthreaded screw hole to a bone which comprises positioning said plate adjacent the bone surface, then inserting a bone screw through said unthreaded screw hole into the bone temporarily to fix said plate to the bone and then securing the plate to the bone by inserting a screw through the threaded screw hole in engagement with the threads in said hole and into engagement with said bone.

* * * * *

UNITED STATES PATENT AND TRADEMARK OFFICE
CERTIFICATE OF CORRECTION

PATENT NO.   : 5,601,553

DATED        : February 11, 1997

INVENTOR(S)  : Linda Trebing & John Thalgott

It is certified that error appears in the above-identified patent and that said Letters Patent is hereby corrected as shown below:

Col. 4, line 56, "metals" should be --metal--.

Col. 6, line 1, claim 12 should depend from claim 11.

Col. 6, line 16, "flat" should be after "intersecting" not before.

Signed and Sealed this

Tenth Day of March, 1998

*Attest:*

BRUCE LEHMAN

*Attesting Officer*   Commissioner of Patents and Trademarks